United States Patent [19]

Oliver

[11] 4,359,727
[45] Nov. 16, 1982

[54] DETECTOR OF DEFECTIVE COATING

[76] Inventor: Gene S. Oliver, 10661 Ponder Way, San Diego, Calif. 92126

[21] Appl. No.: 180,896

[22] Filed: Aug. 25, 1980

[51] Int. Cl.³ ............................................. G08B 21/00
[52] U.S. Cl. .................................... 340/675; 361/180; 200/16 C; 200/61.41
[58] Field of Search ............... 340/657, 675, 676, 677, 340/647, 650; 361/180, 179; 200/61.13, 61.19, 61.41, 61.42, 16 C, 16 D, 177, 178, 16 B; 324/65 R; 427/10

[56] References Cited

U.S. PATENT DOCUMENTS

| | | | |
|---|---|---|---|
| 2,572,597 | 10/1951 | Connor | 324/65 R |
| 2,696,589 | 12/1954 | Bendix et al. | 340/675 X |
| 3,037,163 | 5/1962 | Wiprud | 340/675 X |
| 3,146,431 | 8/1964 | Betts | 200/61.13 X |
| 3,193,630 | 6/1965 | Shlesinger, Jr. | 200/16 B |

Primary Examiner—John W. Caldwell, Sr.
Assistant Examiner—Daniel Myer
Attorney, Agent, or Firm—Finnegan, Henderson, Farabow, Garrett & Dunner

[57] ABSTRACT

A sensor assembly for electrically signalling the presence of bare spots on coated sheet metal for removal before further fabrication.

3 Claims, 7 Drawing Figures

DETECTOR OF DEFECTIVE COATING

BACKGROUND OF THE INVENTION

During the conventional coating of sheet metal small surface areas are sometimes inadvertently allowed to remain uncoated. That is, the coating material, such as enamel, fails to cover the entire sheet leaving small areas of the metal'surface exposed to the atmosphere. Left undetected, such bare spots cause serious problems as rust and other undesirable chemical reactions will result. The canning industry is an example of an activity that cannot afford to make its product from defectively coated sheet metal. Sheets which have bare spots must be detected and removed before fabrication.

Efforts have been made to detect such bare spots. The results have been disappointing. One attempt has been to use electrically charged free-end terminals which contact the coated sheet metal as it moves under the terminals. Proximate terminals carry opposite electrical charges. A current does not normally flow. However, when a bare spot exists between the terminals it causes the sheet metal itself to become a conductor between the terminals. The complete circuit activates means to stop the fabrication machinery so the defective sheet may be removed.

Unfortunately, with protracted use the terminals become bent out of shape and no longer contact the sheet metal. Also, they can only be used on one side of sheets which are often coated on both sides. Until my invention it has been necessary to check each coated side, one after another, rather than both simultaneously.

SUMMARY

I have provided a device that overcomes the shortcomings of the prior art. I replace the free-end contacts with rigid sensor members, secured at both of two ends by spring means. A panel of such members is strong enough to indefinitely remain in proper shape and to contact sheet metal at all times. A panel consists of several strips each carrying a low voltage electrical charge having polarity opposite that of the strip next to it. The strips are of uniform height whereby they support the weight of rapidly moving coated metal sheets passing between a supply stack of sheets and the machinery for fabricating the sheets into a product. Dies for "cupping" the sheets in manufacture of cans is an example. Oppositely disposed like panel of strips may be positioned over the moving sheets and in contact therewith to detect defects in the coating on the upper surface of the sheet at the same time as defects in the underside are being detected. The ability to test both sides of a sheet at one time is an important feature of my invention.

DESCRIPTION OF PREFERRED EMBODIMENTS

Figure 7:
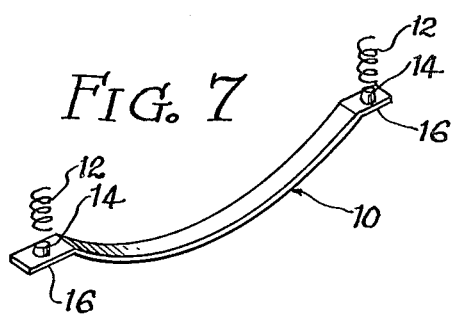
FIG. 7 is a perspective view of a sensor member.

Referring to the accompanying drawing wherein like numerals represent like parts throughout, the numeral 10 is a novel sensor member. It is made of metal for conducting an electrical current. For best results I use rigid strips of arcuate configuration in their central portion with flat end portion for appropriate connections. See FIG. 7. A plurality of such strips are aligned parallel to each other and are spaced sufficiently close to each other, preferably about one-fourth of an inch, to detect an exposed spot 38' coming between them. A panel or set of such sensor members support the weight of light sheets moving over it, eliminating the necessity of "dead plates" over which sheets usually slide on their way from a stack to fabricating machinery. For heavier sheets, additional support means may be used.

Each end 16 of each strip is planar to facilitate its remaining in position at all times. A boss 14 surrounded by a spiral spring 12 is mounted at each end to complete the sensor assembly. The sensors "float" on the springs.

There is a mounting plate 32 with a groove 34 in which the sensor assembly is freely positioned. Also support strip 36 is secured adjacent thereto to support ends 16 which rest thereon when a sheet 38 is not present.

Figure 3:
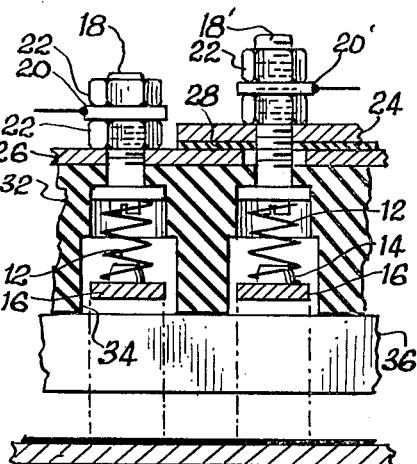
FIG. 3 is a fragmentary sectional view taken along lines 3—3 of FIG. 2.
Figure 4:
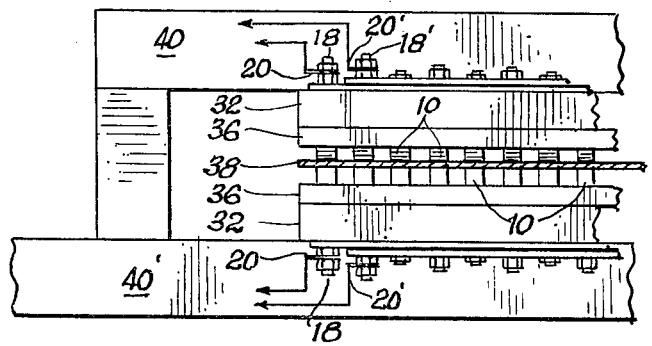
FIG. 4 is a partial side elevational view taken from the left side of FIG. 2.
Figure 5:
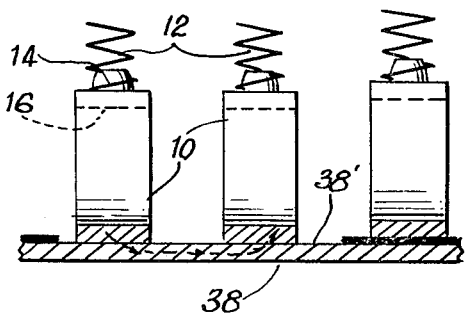
FIG. 5 is a fragmentary cross sectional view through the upper central portion of FIG. 2.
Figure 6:
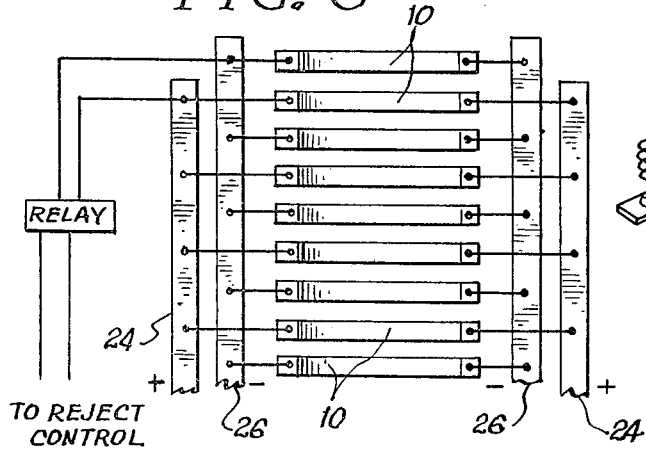
FIG. 6 is a schematic showing the electrical connections between the components.

The end of spring 12 not secured to the sensor, is secured to threaded bolt 18 at its flange head as can best be seen in FIG. 3. The bolt is mounted on buss bar 26, being the lower one in said illustration. Bar 26 has an orifice 30 transversely through its body. Nuts 22 hold the bolt and the end of an electrical wire 20 so that a current may flow from the wire through the bolt and into the sensor with the spring serving as a conduit in the circuit.

Attention is directed to a corresponding longer bolt 18' with its electrical wire terminal 20' similarly mounted. This bolt 18' is parallel to bolt 18 and functions the same except that it carries an opposite electrical charge to that first mentioned. In the later unit, bolt 18' is correspondingly mounted to the upper buss bar 24 of the illustration. Bolt 18' is mounted through orifice 30 without making contact. Contact would result in an electrical short. The buss bars are separated by strip 28 of insulation material. A modification would be the substitution of well-known printed electrical circuits in place of buss bars.

Finally frame 40 and oppositely disposed frame 40' are secured to the mounting plate 32 for retaining the described parts. When two sides of the sheet stock are coated, a double, oppositely disposed detector assembly may be used. When only one side is coated, a single assembly is all that is required.

Figure 1:
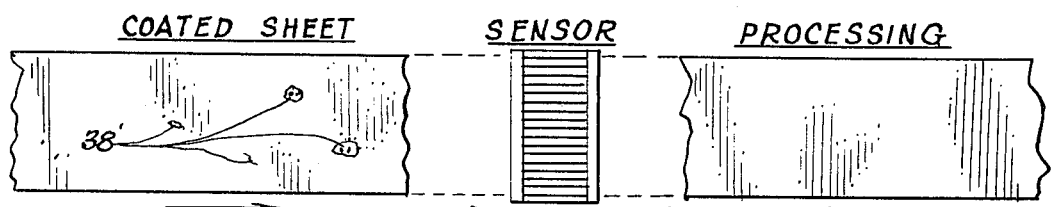
FIG. 1 is a top plan diagram showing the alignment of my invention between the supply stack of sheets and the fabrication equipment.
Figure 2:
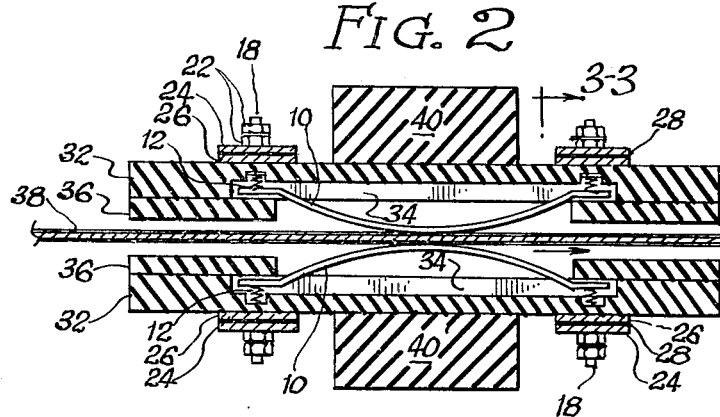
FIG. 2 is a cross sectional side elevation showing a sheet between the double form of my invention.

For use in detecting bare or uncoated spots on enameled sheets in the manufacture of cans, a double assembly, as illustrated, is used because the sheets are enameled on both sides. My novel device is positioned for use between the conventional supply of sheets and the machinery which will press the sheets into a can. See FIG. 1. If a bare, uncoated area exists anywhere on the surface of the sheet, an electrical current will immediately flow from one sensor to the next, activating a relay which stops the power to the machinery. Although the sheets move at a rapid pace and some defects in coating are quite minute, the device causes an immediate halt in the operation so the defective sheet may be removed.

I claim:

1. A detector for detecting defects comprising the absence of an insulated coating on a conductive member passed through the detector, the detector comprising:

a first plurality of electrically conductive guide means transversely positioned with respect to the direction of movement of said member through said detector for supporting said member in an electrically conductive manner;

a second plurality of electrically conductive guide means transversely positioned with respect to the direction of movement of said member through said detector for supporting said member in an electrically conductive manner, each of said first guide means and said second guide means comprising flexible arcuate electrode for tangentially supporting said member passing through said detector, said first guide means and said second guide means being alternately arranged in said positions transverse to the direction of movement of said member:

means for applying an electrical charge of a first polarity to each of said first guide means and a second electrical charge of the opposite polarity to each of said second guide means and means electrically connected to said first guide means and to said second means for detecting a current flowing between a pair of adjacent first guide means and second guide means responsive to an uninsulated area of said member simultaneously electrically contacting one of said first guide means and one of said second guide means.

2. A detector according to claim 1 wherein each of said arcuate electrodes includes straight terminal portions at the ends thereof and wherein said detector further includes a slotted base support for receiving said straight terminal portions of said arcuate electrodes to bias said apexes of said arcuate electrodes against the surface of said member moving through said detector.

3. A detector according to claim 2 further including means for spring mounting said arcuate members in said slotted member.

* * * * *